United States Patent [19]

Rontome et al.

[11] Patent Number: 5,556,480
[45] Date of Patent: Sep. 17, 1996

[54] PROCEDURE FOR DISINFECTING AND CLEANING CONTACT LENSES

[75] Inventors: Carlos P. Rontome; Santiago N. Padilla, both of Madrid, Spain

[73] Assignee: Dirygesa, S.L., Madrid, Spain

[21] Appl. No.: 293,726

[22] Filed: Aug. 22, 1994

Related U.S. Application Data

[63] Continuation-in-part of Ser. No. 879,781, May 6, 1992, abandoned.

[30] Foreign Application Priority Data

May 7, 1991 [ES] Spain ................................. 9101121

[51] Int. Cl.⁶ .......................... B08B 3/00; B08B 7/00
[52] U.S. Cl. .................. 134/26; 134/27; 134/29; 134/42; 422/30
[58] Field of Search .......................... 134/42, 26, 27, 134/28, 29; 427/2.14, 2.21, 2.22, 2.23; 252/99, 174.12; 424/468, 469; 422/30

[56] References Cited

U.S. PATENT DOCUMENTS

| Re. 32,672 | 5/1988 | Huth et al. ............................... 252/95 |
| 3,912,451 | 10/1975 | Gaglia, Jr. ................................. 134/42 |
| 4,585,488 | 4/1986 | Giefer ......................................... 134/27 |
| 4,767,559 | 8/1988 | Kruse et al. .............................. 252/106 |
| 4,775,424 | 10/1988 | Wisotzki et al. .......................... 134/42 |
| 5,011,661 | 4/1991 | Schäfer et al. ............................. 422/30 |
| 5,145,644 | 9/1992 | Park et al. ................................. 422/28 |
| 5,362,647 | 11/1994 | Cook et al. ............................. 435/264 |

FOREIGN PATENT DOCUMENTS

86/01791  11/1986  Spain .

OTHER PUBLICATIONS

Patent No. 86/01791 to Ciba–Geigy AG U.S. Pat. No. 5,011,661.

Primary Examiner—Zeinab El-Arini
Attorney, Agent, or Firm—Collard & Roe, P.C.

[57] ABSTRACT

A procedure for disinfecting and cleaning contact lenses, including introducing the lenses into a container containing therein an aqueous hydrogen peroxide solution and a destabilizer component therefor, prepared in such a way that enables this component to cause controlled peroxide destabilization from the first instance and to maximize its oxidizing action in order to achieve a more efficient lens disinfection and cleaning. As a final result of the process, there is a hydrogen peroxide degradation that results in levels that allow the transformed solution to be compatible with the eye and to maintain the contact lens cleanliness parameters.

20 Claims, No Drawings

PROCEDURE FOR DISINFECTING AND CLEANING CONTACT LENSES

CROSS-REFERENCE TO RELATED APPLICATION

This is a Continuation-in-Part patent application of U.S. patent application Ser. No. 07/879,781 filed May 6, 1992.

BACKGROUND OF THE INVENTION

1. Field of the Invention

The present invention relates to a procedure for disinfecting and cleaning contact lenses, comprising introducing the lenses into a container containing therein an aqueous hydrogen peroxide solution and a destabilizer component therefor in a totally uncoated tablet, prepared in such a way that enables this component to cause controlled peroxide destabilization from the first instance and to maximize its oxidizing action in order to achieve a more efficient lens disinfection and cleaning. As a final result of the process, there is a hydrogen peroxide degradation that results in levels that allow the transformed solution to be compatible with the eye and to maintain the contact lens cleanliness parameters.

2. The Prior Art

Contact lenses in continuous use build up a series of fatty, proteinic, or other kinds of, deposits which act as substrates, allowing environmental microorganisms which are dangerous to the lens itself, and which may even be dangerous to the eye, to be deposited on the substrate. Because of this, several means for disinfecting the lenses have been devised. The most often used procedure is based upon using hydrogen peroxide which possesses a high disinfecting power without damaging the lens morphology, and which leaves no noxious traces once it has been removed.

Using hydrogen peroxide or oxygenated water, however, poses a problem unless it is eliminated once it has concluded its cleaning function, since any trace of this substance on a lens may cause serious irritations to the eye. Thus, the usual procedure consists in first disinfecting the lens with the hydrogen peroxide contained in a suitable container. Then, once the lens has been disinfected, to neutralize the hydrogen peroxide in a second step by any known means, such as chemical compositions, or rinsing with saline water, in such a way that the hydrogen peroxide concentration in the solution is reduced down to a level not damaging to the eye.

It is evident that this two-phase method has the drawback of being slow; and it even implies running the risk on the user's part that the user must adequately oversee completing the process.

In order to overcome this inconvenience, other methods have been further proposed. For example, there is performing the disinfection step and the neutralization step in one method procedure only. That is by introducing the lens into a container simultaneously holding hydrogen peroxide and all the other ingredients required to neutralize it. This will form at the same time an idoneous lens maintenance solution. Also used are methods to delay the neutralizing action by placing layers on the lens which are appropriate substances which will eventually dissolve after some time delay, or other galenic preparation forms as described in the Ciba-Geigy AG patent 86/01791. Some of these prior art forms are very difficult to prepare.

This prior art method, contrary to the present invention, does not seek to increase the hydrogen peroxide oxidative effect, but that by delaying for some previously set time the starting of the neutralizer action, allows lenses to get in contact with the hydrogen peroxide at its maximum although stabilized concentration. It is after the above-mentioned previously set time when the total neutralizer is released in a fast manner, thus destroying hydrogen peroxide in order that the lens will cause no harm to the eye.

Thus, the only apparent reason for including a neutralizer herein is to destroy the excess hydrogen peroxide.

other methods for the one-step procedure to neutralize hydrogen peroxide are to employ heavy metals as catalysts, such as platinum, which performs a slow neutralization, whereby the catalytic activity is reduced as the peroxide concentration is reduced. This prior art procedure is described in the Gaglia U.S. Pat. No. 3,912,451 of Oct. 14, 1975.

This method clearly differs from the present invention which achieves improved results. According to this prior art patent, contact lenses are submerged in normally stabilized hydrogen peroxide in order to have them disinfected through its standard action.

Simultaneously, or some time thereafter, a support holding a metal-type catalyst is submerged into the solution in order to start destroying the hydrogen peroxide by releasing oxygen, thus obtaining peroxide concentrations in the solution which are unable to cause eye discomfort once the contact lens has been inserted.

There is no hydrogen peroxide activation in this prior art system. On the contrary, oxygen is only released at the metal catalyst surface, forming no complex at all, and this generated oxidizing is recombined to form an oxygen molecule whose oxidative power is very low. Therefore, the hydrogen peroxide solution in the prior art is not being selectively activated, whereas in the present invention, it is selectively activated. In the prior art method, it is being deactivated. It is apparent that no other result is sought in the prior art other than eliminating hydrogen peroxide from the contact lens after disinfecting it, and that this elimination is obtained by means of a metal catalyst.

In the prior art, other single-step, single-phase methods exist which, by using physical hindrances for releasing the neutralizer, would delay the hydrogen peroxide degradation. Up to this time it has always been thought that stabilizing the peroxide concentration would always be enough during the time interval required for the peroxide to perform its disinfecting action.

SUMMARY OF THE INVENTION

The present invention is an improvement over the prior art, because it will improve hydrogen peroxide solution qualities in order that, when activating it, its cleaning action will be faster and more efficient.

It is therefore an object of the present invention to provide a hydrogen peroxide disinfecting action based on oxidation taking place on the microorganism membranes until it destroys them. This oxidation is performed by generating oxygen formed as a result of peroxide decomposition:

$$H_2O_2 \longrightarrow H_2O + O$$

Hydrogen peroxide is composed of two hydrogen atoms and two oxygen atoms. These atoms are linked through covalent bonds sharing one pair of electrons between hydrogen and oxygen atoms. Because of the water molecule configuration and the closer proximity of the electrons to the oxygen nucleus, the hydrogen becomes oxidized and partially loses its electron, which is then gained by oxygen. Thus, it may be theorized, therefore, that the $H_2O_2$ molecule is ionized, constituted by an $O_2$ anion and two $H^+$ cations. Metal peroxide reactions, such as $NaO_2$ and $BaO_2$, with strong acids such as hydrochloric or sulfuric, demonstrate that the $O_2$ group (peroxide ion) may actually exist in solution.

Hydrogen peroxide may act as an oxidizing agent or as a reducing agent due to the fact that the peroxide ion exists in an intermediate state located between free molecular oxygen and oxide oxygen. The peroxide ion may lose two electrons and become oxidized to produce free oxygen, or either the peroxide ion can gain electrons and become reduced to two oxide oxygens.

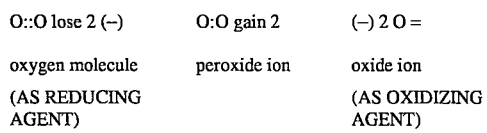

| O::O lose 2 (–) | O:O gain 2 | (–) 2 O = |
|---|---|---|
| oxygen molecule | peroxide ion | oxide ion |
| (AS REDUCING AGENT) | | (AS OXIDIZING AGENT) |

Due to this double character as oxidizer-reducer, it happens that an $H_2O_2$ molecule may act as an oxidizing agent for another similar molecule which would act as a reducing agent, thus producing water and free oxygen.

$$2H_2O_2 = 2H_2O + O_2 + 46{,}200 \text{ calories}$$

Since molecules tend to reside at the lowest energy levels and this being an exothermic reaction, there is a tendency in this reaction for the equilibrium to shift to the right, and for hydrogen peroxide to decompose to yield molecular oxygen and water.

While this reaction can take place spontaneously in a slow manner, it can be affected by factors accelerating the reaction rate, such as light, alkali, or dust particles, etc. Thus, commercially marketed hydrogen peroxide solutions are usually stabilized with suitable additives and in an acid medium.

These stabilized solutions are those used for disinfecting. Although they have a remarkable germicidal power, their oxidizing reaction rate in an acid medium is very slow. Therefore, by starting from a stabilized hydrogen peroxide solution, it is possible to obtain a destabilized level at the time of using it, so as to obtain an "activated" peroxide having much higher oxidizing power.

If a small quantity of a catalytic enzyme, for instance, catalase, is introduced, then a complex is formed between the hydrogen peroxide and the enzyme:

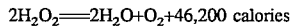

$$H_2O_2 + \text{enzyme} \longrightarrow (H_2O_2 * \text{enzyme})$$

In this complex, bonding of the oxygen linked with water is at a maximum. However, if the solution should contain some destabilizing factor, such as proteins, container physical irregularities or foreign particles, etc., these factors will be sufficient to act as nucleation sites for the complex, and to generate oxygen in situ:

$$(H_2O_2 * \text{enzyme}) + \text{factor} \longrightarrow H_2O + \text{enzyme} + \text{factor} - O$$

Thus, a solution is obtained in which the complex, which may react at any point, is dissolved throughout the entire solution.

The following reaction may also occur:

$$(H_2O_2 * \text{enzyme}) + (H_2O_2 * \text{enzyme}) \longrightarrow 2H_2O + O_2 + 2 \text{ enzyme}$$

and all of it at the activation factor nucleation site. It is possible to visually check and determine that it is on those sites where oxygen is released that the greatest oxidizing action is taking place.

This may be physically seen in a clearly demonstrative manner, by comparison, based upon the preparation of two aqueous hydrogen peroxide solutions. The first one (A) is an aqueous 3% hydrogen peroxide solution, for instance, stabilized with 0.1% disodium EDTA, for example. The second one (B) is the same as solution (A) to which has been added enough enzyme, for instance 400 U.K. catalase, to obtain the necessary destabilization and relevant complex formation. If into both solutions a glass strip is submerged, and onto which strip some protein (for instance, denatured egg albumin bonded by heat) has been placed, the following result is observed. On that strip submerged in the (A) solution container, no apparent reaction phenomena take place. On the strip submerged in the (B) solution, oxygen bubbles start forming immediately, and especially on the surface wherein the protein has been placed.

This is due to the immediate reaction attack by the generated oxygen as it is being released from the complex ($H_2O_2$ * enzyme) in the presence of the protein in the (B) solution. While in the (A) solution, where no complex has been formed, the mere presence of protein is unable to release any oxygen, even after a reasonably long time.

It is known that protein is one of the products helping to decompose hydrogen peroxide, and thus, there is a greater ease with which protein is attacked by oxygen released by peroxide decomposition. Therefore, since proteins form a part of the microorganism cell walls and other cellular structures thereof, these microorganisms are destroyed in the presence of oxygen from hydrogen peroxide.

One more demonstrated example of the activation taking place in aqueous peroxide solution when it is destabilized is the rapid destruction of bacteria having catalase in this solution. As pointed out above, this is due to the immediate formation of generated oxygen taking place on these bacteria.

It can be demonstrated that the lethal killing power of an "activated" aqueous hydrogen peroxide solution upon these microorganisms is higher than that of a normally stabilized solution. To ascertain this, a comparative test was chosen to determine the effect of solutions (A) and (B) on a resistant microorganism in order to have a demonstrative test. The microorganism *Candida utilis* yeast was chosen with a concentration initially of $2 \times 10^5$ microorganisms per ml of solution. The test results are as follows:

TABLE I

| | Viability - Survival Rate per ml | |
|---|---|---|
| Time | Solution (A) | Solution (B) |
| 0 | $2 \times 10^5$ | $2 \times 10^5$ |
| 2 min. | $9.5 \times 10^4$ | $4 \times 10^4$ |
| 5 min. | $3 \times 10^4$ | $7 \times 10^3$ |
| 15 min. | $1.8 \times 10^3$ | $4 \times 10^2$ |

D (time required to lower the viable concentration in one logarithmic unit) is 4.9 minutes for solution (A) and 1.8 minutes for solution (B).

It is clear from the results set forth in Table I above that activated hydrogen peroxide has its germicidal power increased and, as it may be seen in this Table, its germ-killing power during the time it acts is 2.5 to 4.5 times greater.

Not only does "activated" hydrogen peroxide according to the invention have its germicidal power increased, but in addition, it is much more efficient at destroying dirt deposits built up on contact lens surfaces. This is logical, since the activated hydrogen peroxide aqueous solution selectively releases generated oxygen, in an immediate manner, in those dirty places, which is where the complex ($H_2O_2$ * enzyme) is destroyed. In this way, a strong oxidizing reaction takes place exactly on the spot where it is required. Consequently, it destroys the dirt deposit structure, which is easily dissolved within the surrounding solution, which is aided by the convective circulation taking place at the oxygen release site.

The following test has been performed:

100 glass strips measuring approximately 60×10 mm are submerged in an 0.2% egg white (albumin) solution bath for 15 minutes. Once this time has elapsed, the strips are removed and transported into a dry heat stove at 140° C., leaving them there for 30 minutes to bond the protein through heat to the glass. The protein coating formation was evaluated by selecting 24 homogeneously coated strips.

Four of the protein-coated strips were submerged in a saline solution (Fisiozor of Laboratorios Avizor). Ten of the protein-coated strips were placed in solution (A) (3% hydrogen peroxide solution stabilized with 0.1% disodium EDTA). The remaining ten were submerged in solution (B) (solution (A) with the addition of 400 U.K. catalase as destabilizer). The strips were taken out half an hour later, rinsed with saline solution, and their cleanliness status was evaluated.

All ten samples treated with solution (A) showed a cleanliness status higher than that of the four blank samples. Protein coating remained in both cases on 100 percent of their surfaces. Protein coating had disappeared from between 70% to 85% of the surface area of the samples treated with solution (B).

Having available an activated hydrogen peroxide possessing high oxygen mobility provides a major improvement in contact lens maintenance, since as lens care operations are performed in relatively short periods of time, highly efficient disinfecting and cleaning products are provided. Although stabilized peroxide has a certain germicidal power in a short time, its removal action on dirt deposits on the lens surface during the cleaning period during which these maintenances are performed is practically nil.

On the contrary, with the system and process according to the invention, besides increasing the germicidal killing power, its activity for removal of dirt is enormously increased. The activated peroxide solution can readily clean a lens within the short time span allotted for using the system.

With this system according to the invention there is a substantial advantage over those existing prior art cleaning systems. With regard to those prior art systems requiring two cleaning phases, the present invention has the advantages regarding eye comfort discussed above, as well as avoiding dangerous prior art mistakes. Compared with those prior art systems comprising only one cleaning phase, the present invention has the advantage based upon quicker performance time, safer neutralization and lower cost.

As regards other single-phase prior art systems, the present invention has all those inherent advantages already discussed. In addition, the present invention will allow lenses to be free of any chemical preservative. The resulting solution according to the invention is free of preservatives which are not required, since by performing the method of the invention, germs are eliminated and, since it can be performed in a closed container, lenses will remain aseptic, provided the container is not opened.

However, in any case, the unique properties of the claimed method provide unexpected results with regard to all other methods based on the fact that the inventive procedure uses activated hydrogen peroxide, which destroys germs at a much faster rate; and since it has oxygen available throughout the entire cleaning process, it is able to completely obliterate the microorganisms.

Whereas the prior art peroxide systems scarcely reach any significant levels of cleaning, the inventive procedure achieves levels of cleanliness and sterility high enough to usually make unnecessary using any other cleaning products to keep these lenses at an optimum wearing preservation state.

The system and method of operation according to the invention will clean, disinfect and preserve contact lenses comprising submerging them in a container, wherein an aqueous $H_2O_2$ solution having an effective concentration, for instance, between 0.5% and 6% by weight based upon the total solution weight, has been poured. It may reach aseptical action levels within a short period of time, preferably 10–15 minutes, with a 3% by weight peroxide concentration based upon the total weight of the solution. Also, from the beginning, there is a peroxidase-type catalytic enzyme, catalase for instance, introduced in solid form (granules, tablets, etc.) or in liquid form into the solution, and disposed in such a way as to be continuously, although slowly, released so that complex ($H_2O_2$ * enzyme) formation takes place in the solution to give rise to peroxide activation. It does not matter for how long lenses are submerged in the solution while the process is taking place, although it is advisable that it should last, due to user's comfort reasons, between half an hour and two hours.

Continuous enzyme release may be graduated in order that within the time period selected, an oxygen volume be released so that residual hydrogen peroxide concentration will be lower than 50 ppm, for instance. This is a limit within which hydrogen peroxide causes no irritation to the human eye, although even full peroxide degradation may be reached at this concentration level.

The procedure according to the invention comprises submerging contact lenses in an aqueous hydrogen peroxide solution having adequate concentration, with the residence time being selected for disinfecting and sterilizing the lens. The hydrogen peroxide is activated by destabilization produced by gradual release, from the beginning, of a catalyst. Throughout the residence time selected, the catalyst release is able to reduce the hydrogen peroxide residual levels below the limits which could cause discomfort to the eye of the wearer if it were contacted with the residual levels in solution.

Releasing of the catalyst in a controlled manner from the beginning may be performed in many ways.

As examples, the catalyst may be provided in the form of a totally uncoated tablet or non-coated pellet containing, together with the catalyst enzyme, other ingredients to obtain a resulting solution have an idoneous pH and osmotic qualities to maintain the lenses at the desired parameters of cleanliness and sterility. Other useful ingredients include boric acid and its salts, phosphates, as well as alkali metal chlorides, disodium EDTA and other suitable agents.

In one embodiment, the totally uncoated non-coated tablet or granule could be constructed in such a way as to have a catalyst concentration gradient with the lower concentration being present on its surface and with a higher catalyst concentration being present in its nucleus. These tablets will have the catalyst held in the outer portion by slightly soluble products which are slow to dissolve, such as polyvinylpyrrolidones, polyacrylic acid, cellulose by-products, etc., and that the tablet nucleus will have its catalyst held by more highly soluble products.

In another embodiment, the tablet, after having been made, could be subject to treatments which decrease the enzyme activity in a selective manner such as, for instance, with dry heat or with wet heat or with products partially deactivating the catalyst, such as short chain alcohols, for example, ethanol. As an example, the totally uncoated non-coated tablet may contain an acid pH on this outside surface which will cause the enzyme therein to be partially destroyed, thus delaying the tablet dissolution. A tablet of this kind may be made by forming a nucleus wherein the enzyme is mixed with the coadjuvants for maintaining the pH and the osmotic pressure, and then by covering the nucleus with innocuous acids such as tartaric acid or adipic acid.

In a further embodiment, it is possible to produce a totally uncoated non-coated tablet not having a gradual time release action, but instead, to have a stepped function release action. To this end, a tablet, or any other galenic form, is made with three concentric layers. The outermost layer holds a quantity of enzyme sufficient to achieve the formation of the complex activating the hydrogen peroxide. The middle layer is neutral and containing no enzyme, it serves the purpose of taking that much time to dissolve which is the time lapse chosen to enable the complex to act. Once this middle layer is dissolved, the solution comes into contact with the innermost layer, which contains the required catalyst to continue forming the active complex and simultaneously deactivating the peroxide down to a level which is not irritating to the eye of the lens wearer.

In manufacturing this totally uncoated non-coated tablet, the outer layer may be made out of a mixture of above-mentioned ingredients to obtain a correct final pH, or to prepare the soluble material integrally containing the catalyst.

The middle layer may be prepared from ingredients which can be used to cover the nucleus, or which may be materials difficult to dissolve, such as acrylic polymers, polyethyleneglycols, cellulose by-products, polyvinylpyrolidones, etc., or small crystallizing molecular products as well, such as sodium chloride or boric acid and its salts. Thus, a nucleated tablet may be made without resorting to coatings.

In another embodiment, there are process steps which result in partially destabilizing the hydrogen peroxide in order to obtain a higher activity thereof. Thus, the peroxide becomes unstable when the solution pH is increased up to basic values above 7, and preferably above 10. This happens for the same reason as is found due to the chemical-physical phenomena that occurs in forming the complex ($H_2O_2$ * enzyme). This reason is because the activation energy required for decomposing the hydrogen peroxide decreases. Therefore, those substances which under standard conditions would take a long time in decomposing it, would decompose it now, thus giving rise to local oxidizing phenomena which performs the above-described effects. Thus, it can be seen that by increasing the pH to high basic values, oxygen labilization and mobility are obtained and this may act with a higher oxidizing power throughout the entire disinfection process.

The system according to the invention could be made, for instance, by placing lenses within a container together with the aqueous hydrogen peroxide solution and totally uncoated non-coated tablet having two concentric layers. This tablet would have as the inner layer a peroxide neutralizer together with, besides other coadjuvant products, the acidic ingredient. The outer layer would contain at least the basic ingredient. Both layers may either be separable or inseparable. Thus, it is possible to delay the action of the peroxide neutralizer down to required levels.

This system according to the invention has a much higher germicidal and cleaning power than that of other systems based on time-delay coated tablets which only seek further neutralizer activity.

Other objects and features of the present invention will become apparent from the following detailed description considered in connection with the accompanying example which discloses one embodiment of the present invention. It should be understood, however, that the example is designed for the purpose of illustration only and not as a definition of the limits of the invention.

DETAILED DESCRIPTION OF THE PREFERRED EMBODIMENT

The procedure to disinfect and clean contact lenses is fundamentally carried out by a combination of two ingredients. The first ingredient is an aqueous hydrogen peroxide solution, preferably having 0.3% to 3% by weight of hydrogen peroxide based upon the total solution weight. The second ingredient is a catalyst being capable of forming an active complex with hydrogen peroxide, which catalyst is preferably catalase. It has been discussed above that this catalyst will be prepared as a totally uncoated non-coated tablet, capsule or any other galenic form, either as the only component thereof or together with other complementary ingredients to complete the lens maintenance process.

Hence, the disinfecting and cleaning procedure according to the invention comprises submerging the lenses in a container holding, at the same time, an aqueous hydrogen peroxide solution and a totally non-coated uncoated tablet containing the enzymatic catalyst located in a special manner therewithin, allowing the tablet to successively release the catalyst, and thus activate the peroxide. Thus, the peroxide can act to disinfect and clean the lens. When the tablet has fully dissolved, the volume of enzymatic catalyst released will be such that it may degrade, during the established time lapse, the entire amount of peroxide present in the solution. The hydrogen peroxide will have been transformed due to the addition to the solution of the other ingredients into a regulated pH and osmolality solution similar to that of human tears. This cleansing solution will maintain the lens sterility at acceptable parameter levels and will be compatible with the eye.

Furthermore, the user may keep the lens stored in its closed container for as long as the user desires.

The process has been designed to require a total cleaning and disinfecting time of about half an hour to two hours, although other time intervals may be chosen.

For performing the method according to the invention, a totally non-coated uncoated tablet may be preferably made having a nucleus and an outer portion. The nucleus would contain the catalase, which is present in an amount sufficient to determine the peroxide degradation. The nucleus could contain, as well, a part of the other ingredients used for obtaining the pH and osmolality desired. These ingredients could, for example, be boric acid and sodium tetraborate, monosodium and disodium phosphates, sodium chloride, potassium chloride, disodium EDTA and other excipients. The outer portion could contain enough quantity of catalase to destabilize the hydrogen peroxide and form an active complex. The outer portion may also contain ingredients similar to those it carries in its nucleus, such as sodium chloride and boric acid, and it may contain, as well, other components making its solubility occur at a slower rate, such as polymers, for example, polyvinylpyrolidone, polyacrylic acid, and/or polyethyleneglycol.

It is not considered necessary to make this description any longer for any expert in this matter to understand the invention and the advantages obtained therefrom. The terms under which this specification has been described should be taken at all times in their broadest, non-limitative sense.

While several embodiments of the present invention have been shown and described, it is to be understood that many changes and modifications may be made thereunto without departing from the spirit and scope of the invention as defined in the appended claims.

What is claimed is:

1. A process for cleaning and disinfecting contact lenses to be worn in contact with an eye, comprising submerging a contact lens in a container containing an aqueous solution of hydrogen peroxide and a totally non-coated tablet form;

producing initially a controlled destabilizing of the hydrogen peroxide using a destabilizer in order to obtain an activation thereof due to increased oxygen lability and mobility throughout the whole solution, with consequent increase of its germicide and cleaning effects; and reducing by degradation of the hydrogen peroxide a concentration of hydrogen peroxide down to a level allowing the solution to be compatible with the eye.

2. The process for cleaning and disinfecting contact lenses according to claim 1, wherein hydrogen peroxide destabilizing is obtained by means of a catalyst.

3. The process for cleaning and disinfecting contact lenses according to claim 2, wherein the catalyst is an enzymatic catalyst.

4. The process for cleaning and disinfecting contact lenses according to claim 3, wherein the enzymatic catalyst is catalase.

5. The process for cleaning and disinfecting contact lenses according to claim 3, wherein the enzymatic catalyst is a mixture of several peroxidases.

6. The process for cleaning and disinfecting contact lenses according to claim 1, wherein peroxide destabilizing is obtained by increasing solution pH.

7. The process for cleaning and disinfecting contact lenses according to claim 1, wherein time for said controlled destabilizing constitutes a full lens disinfecting time or a major part of it.

8. The process for cleaning and disinfecting contact lenses according to claim 1, comprising dissolving the destabilizer initially and in a fast manner with the destabilizer being located in a totally non-coated tablet outer portion.

9. The process for cleaning and disinfecting contact lenses according to claim 1, comprising providing the destabilizer initially in a slow manner to the solution, as it is gradually dissolved out of the totally non-coated tablet, and said destabilizer being incorporated in a uniform manner into the totally non-coated tablet.

10. The process for cleaning and disinfecting contact lenses according to claim 1, further comprising a neutralizer; and wherein the destabilizer, which may be same substance as the neutralizer, is distributed within the totally non-coated tablet in a non-uniform manner, with the totally non-coated tablet having a concentration gradient such that a destabilizer concentration increases towards a center of the totally non-coated tablet.

11. The process for cleaning and disinfecting contact lenses according to claim 10, wherein both peroxide destabilizer and neutralizer are the same substance, catalase.

12. The process for cleaning and disinfecting contact lenses according to claim 1, wherein the destabilizer is a mixture of peroxidase and basifying products which increase solution pH.

13. The process for cleaning and disinfecting contact lenses according to claim 1, wherein during a time that the destabilizer is acting, a sufficient amount of material to neutralize the peroxide is dissolved out from remaining tablet components, during a time interval which is sufficient to disinfect the lens.

14. The process for cleaning and disinfecting contact lenses according to claim 1, wherein the totally non-coated tablet contains other components which increase the germicide and cleaning effect of the solution.

15. The process for cleaning and disinfecting contact lenses according to claim 1, wherein after a cleaning and disinfecting period is over, using a peroxide degrading substance which continues acting, or comes for a first time into contact with the solution, in order to produce decomposition of remaining peroxide without becoming neutralized by either water or the oxygen, until a residual peroxide reaches a level compatible with the eye.

16. The process for cleaning and disinfecting contact lenses according to claim 15, wherein a residual peroxide level is equal to or lesser than 50 ppm.

17. The process for cleaning and disinfecting contact lenses according to claim 1, wherein the totally non-coated tablet contains a salt concentration sufficient to stabilize pH of the solution at end of the cleaning and disinfecting process.

18. The process for cleaning and disinfecting contact lenses according to claim 17, wherein at the end of the cleaning and disinfecting process, the solution pH ranges from 6 to 8.

19. The process for cleaning and disinfecting contact lenses according to claim 18, wherein at the end of the cleaning and disinfecting process, the solution pH ranges from 6.5 to 7.5.

20. The process for cleaning and disinfecting contact lenses according to claim 1, wherein tablet components cause the solution to have a tonicity equal to that of human eye tears.

* * * * *